(12) United States Patent
Loyen

(10) Patent No.: US 9,764,167 B2
(45) Date of Patent: Sep. 19, 2017

(54) METHOD FOR PRODUCING FREE POWDER PARTICLES OF POLYAMIDE IMPREGNATED WITH AT LEAST ONE COSMETIC OR PHARMACEUTICAL AGENT, AND FREE POWDER PARTICLES OF POLYAMIDE HAVING A CONTENT OF AT LEAST 25 WT % OF A COSMETIC OR PHARMACEUTICAL AGENT OTHER THAN WATER

(75) Inventor: Karine Loyen, Pont-Audemer (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 13/265,420

(22) PCT Filed: Apr. 16, 2010

(86) PCT No.: PCT/FR2010/050740
§ 371 (c)(1),
(2), (4) Date: Dec. 19, 2011

(87) PCT Pub. No.: WO2010/122258
PCT Pub. Date: Oct. 28, 2010

(65) Prior Publication Data
US 2012/0093901 A1    Apr. 19, 2012

(30) Foreign Application Priority Data

Apr. 21, 2009   (FR) ..................... 09 52579

(51) Int. Cl.
*A61K 8/88*    (2006.01)
*A61Q 9/04*    (2006.01)
(Continued)

(52) U.S. Cl.
CPC ............. *A61Q 1/14* (2013.01); *A61K 8/0241* (2013.01); *A61K 8/0279* (2013.01); *A61K 8/365* (2013.01);
(Continued)

(58) Field of Classification Search
CPC ............ A61Q 1/14; A61Q 1/00; A61Q 13/00; A61K 8/88; A61K 8/68; A61K 8/65;
(Continued)

(56) References Cited

U.S. PATENT DOCUMENTS 4,720,489 A    1/1988   Shander
4,885,289 A    12/1989  Breuer et al.
(Continued)

FOREIGN PATENT DOCUMENTS

FR          2692781 A1 * 12/1993
WO   WO 2009/100962 A1 *  8/2009

OTHER PUBLICATIONS

Polyamide 6/12—Nylon 6/12—PA 6/12: retrieved from internet: http://www.azom.com/article.aspx?ArticleID=468. Retrieved on Oct. 25, 2013.*

(Continued)

*Primary Examiner* — Hong Yu
(74) *Attorney, Agent, or Firm* — Millen, White, Zelano & Branigan, P.C.

(57) ABSTRACT

The invention relates to a method for producing free powder particles of polyamide, impregnated with at least one cosmetic or pharmaceutical agent. The present invention also relates to free powder particles of polyamide having a content of at least 25% by weight of a cosmetic or pharmaceutical agent other than water, to the use of said particles in a cosmetic, pharmaceutical or perfumery products, and to compositions containing such particles.

20 Claims, 1 Drawing Sheet

(51) Int. Cl.

| | | |
|---|---|---|
| *A61K 9/14* | (2006.01) | |
| *A61Q 17/04* | (2006.01) | |
| *A61Q 5/08* | (2006.01) | |
| *A61Q 1/02* | (2006.01) | |
| *A61Q 1/06* | (2006.01) | |
| *A61Q 15/00* | (2006.01) | |
| *A61Q 5/06* | (2006.01) | |
| *B05D 7/02* | (2006.01) | |
| *A61Q 5/02* | (2006.01) | |
| *A61Q 19/10* | (2006.01) | |
| *A61Q 1/14* | (2006.01) | |
| *A61Q 1/00* | (2006.01) | |
| *A61Q 13/00* | (2006.01) | |
| *A61K 8/365* | (2006.01) | |
| *A61K 8/68* | (2006.01) | |
| *A61K 8/02* | (2006.01) | |

(52) U.S. Cl.
CPC ............... *A61K 8/68* (2013.01); *A61K 8/88* (2013.01); *A61Q 1/00* (2013.01); *A61Q 13/00* (2013.01); *A61K 2800/412* (2013.01); *A61K 2800/56* (2013.01)

(58) Field of Classification Search
CPC ............... A61K 8/0241; A61K 8/0279; A61K 2800/56; A61K 2800/412
USPC ....... 424/401, 489, 59, 62–65, 70.17; 8/405, 8/161; 427/2.14, 222; 510/126, 130, 510/136; 512/4
See application file for complete search history.

(56) References Cited

U.S. PATENT DOCUMENTS

| | | | |
|---|---|---|---|
| 5,095,007 | A | 3/1992 | Ahluwalia |
| 5,096,911 | A | 3/1992 | Ahluwalia et al. |
| 5,132,293 | A | 7/1992 | Shander et al. |
| 5,143,925 | A | 9/1992 | Shander et al. |
| 5,292,512 | A | 3/1994 | Schaefer et al. |
| 5,328,686 | A | 7/1994 | Shander et al. |
| 5,358,719 | A | 10/1994 | Mellul et al. |
| 5,364,885 | A | 11/1994 | Ahluwalia et al. |
| 5,411,991 | A | 5/1995 | Shander et al. |
| 5,440,090 | A | 8/1995 | Davis et al. |
| 5,455,608 | A | 10/1995 | Stewart et al. |
| 5,468,476 | A | 11/1995 | Ahluwalia et al. |
| 5,475,763 | A | 12/1995 | Kaufman et al. |
| 5,648,394 | A | 7/1997 | Boxall et al. |
| 5,652,273 | A | 7/1997 | Henry et al. |
| 5,674,477 | A | 10/1997 | Ahluwalia |
| 5,728,736 | A | 3/1998 | Shander et al. |
| 6,020,006 | A | 2/2000 | Styczynski et al. |
| 6,075,052 | A | 6/2000 | Suzuki et al. |
| 6,171,595 | B1 | 1/2001 | Suzuki et al. |
| 6,239,170 | B1 | 5/2001 | Ahluwalia et al. |
| 6,355,686 | B1 | 3/2002 | Bajor et al. |
| 6,355,687 | B1 | 3/2002 | Bajor et al. |
| 6,375,948 | B1 | 4/2002 | Tsuji et al. |
| 6,407,056 | B1 | 6/2002 | Seiberg et al. |
| 6,414,017 | B2 | 7/2002 | Ahluwalia et al. |
| 6,565,834 | B2 | 5/2003 | Kini et al. |
| 6,663,962 | B2 | 12/2003 | Le Crom et al. |
| 7,968,607 | B2 | 6/2011 | Nishijima et al. |
| 2005/0031699 | A1* | 2/2005 | Simonnet ................. A61K 8/25 424/489 |
| 2006/0115504 | A1* | 6/2006 | Loyen .................... A61K 8/064 424/401 |
| 2008/0274149 | A1* | 11/2008 | Seiler et al. .................. 424/401 |
| 2009/0018200 | A1* | 1/2009 | Willemin et al. ............. 514/576 |
| 2009/0047316 | A1 | 2/2009 | Simonnet et al. |
| 2009/0263434 | A1 | 10/2009 | Shoji et al. |
| 2011/0021409 | A1* | 1/2011 | Cox ....................... C11D 3/3719 510/349 |

OTHER PUBLICATIONS

Orgasol 2002 N5HY Cos: retrieved from internet: http://dir.cosmeticsandtoiletries.com/detail/tradeName.html?id=17046. retrieved on Jan. 15, 2016.*

Hyaluronic acid, sodium salt: retrieved frominternet: http://ornatural.com/chi/pdf/detox-firm/Sodium%20Hyaluronate.pdf. Retrieved on Jan. 19, 2016.*

Spheroidal: retrieved from internet: http://www.thefreedictionary.com/spheroida. retrieved on Jan. 19, 2016.*

"Orgasol® cosmetic ingredients", Arkema, (2008), p. 2. From Internet.

* cited by examiner

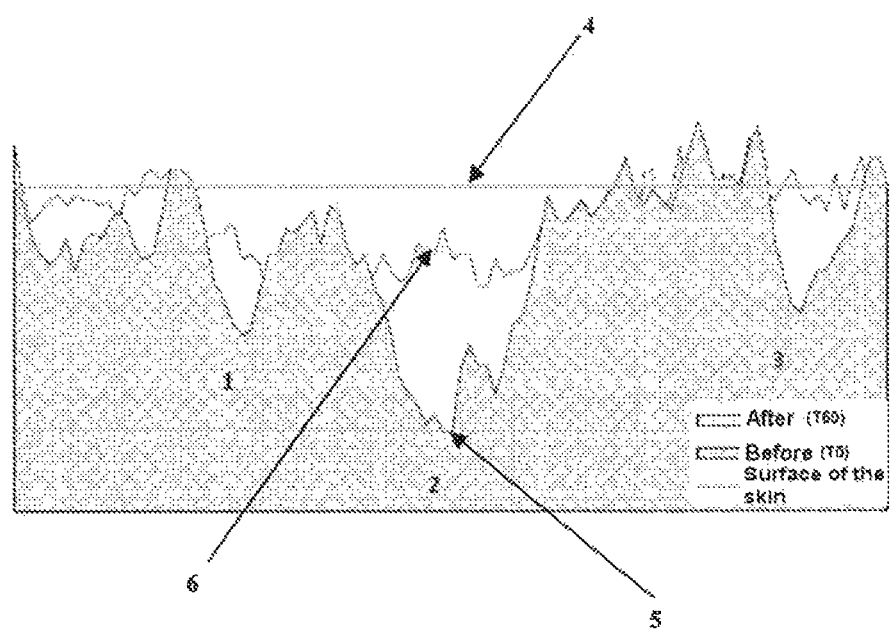

METHOD FOR PRODUCING FREE POWDER PARTICLES OF POLYAMIDE IMPREGNATED WITH AT LEAST ONE COSMETIC OR PHARMACEUTICAL AGENT, AND FREE POWDER PARTICLES OF POLYAMIDE HAVING A CONTENT OF AT LEAST 25 WT % OF A COSMETIC OR PHARMACEUTICAL AGENT OTHER THAN WATER

The present invention relates to a process for the manufacture of particles of free polyamide-based powder impregnated with at least one cosmetic or pharmaceutical agent. The present invention relates in particular to particles of free polyamide-based powder having a content of at least 25% by weight of at least one cosmetic or pharmaceutical agent other than water.

The invention also relates to the use of these particles comprising a high content of cosmetic or pharmaceutical agent in cosmetic, pharmaceutical or perfumery products and to the cosmetic, pharmaceutical or perfumery compositions comprising such particles.

Numerous examples are known of cosmetic or dermatological compositions intended for the treatment of the skin, exhibiting one or more active principles suitable for the treatment of the skin, encapsulated in phospholipid microsphere or lipid vesicles (also known as liposomes) or in polymer microspheres, for example described in document EP 0 375 520. The drawbacks of these encapsulation techniques are the difficulty in controlling the process of manufacture of the microspheres and their lack of stability during their storage or when they are introduced into cosmetic formulations. Generally, the amount of active principle(s) introduced during the manufacture of the microspheres differs from the amount (lower) which remains in the microspheres during their storage and also differs from the amount (even lower) released on the akin.

Patent application EP 1 493 433 describes porous particles comprising at least one active compound. These particles are obtained by a process which consists in impregnating porous particles with at least one active compound solubilized beforehand in a solvent, such as acetone, ethanol, isopropanol, dichlormethane, or ethyl acetate, then evaporating the solvent until a dry powder is obtained. However, a proportion, even small; of these solvents is always re-encountered in the powders obtained and in the finished products which incorporate these powders. In point of fact, these solvents are the cause of undesirable effects on the skin, such as dryness, allergies, pigmentation, and the like.

The commercial brochure "Orgasol® Poudre polyamide ultra fine", dating from February 1991, and the ORGASOL IMPREGNES range described in the review "Cosmetic and Toiletries", volume 108, which appeared in December 1993, have priority over the abovementioned patent application. The brochure and the review describe in particular the impregnation of Orgasol® (porous polyamide 12 powder) by a cosmetic active principle solubilized in a solvent which is subsequently generally evaporated. The final level of cosmetic or pharmaceutical agent in these impregnated powders does not exceed 20%.

An aim of the present invention is thus to provide a process for manufacture of particles of free powder which are highly charged with cosmetic or pharmaceutical agents which does not exhibit the disadvantages of the prior art, which avoids the presence of solvents harmful to the skin, which exhibits the fewest possible stages and which does not detrimentally affect the cosmetic or pharmaceutical properties of these agents.

Another aim of the present invention is to provide particles of free powder which are highly charged with cosmetic or pharmaceutical agents, for which the amount of agents remains stable during the storage of the particles and when they are incorporated in a formulation, and for which the diffusion of these agents into the stratum corneum of the skin is improved, that is to say enhanced and/or prolonged after topical application of these particles to the skin. The term "particles of free powder which are highly charged with cosmetic or pharmaceutical agent(s)" is understood to mean particle having a content of at least 25% by weight, preferably at least 40% by weight, of this (or these) agent(s).

It has now been shown that it is possible to manufacture such particles of free powder which are highly charged with cosmetic or pharmaceutical agents by virtue of a novel process of impregnation of porous particles.

The expression "porous particles" is intended to denote particles comprising pores. The porosity is characterized quantitatively by the specific surface (also known as SS). The porous particles of the invention exhibit an SSA, measured according to the BET method, of greater than or equal to $8\ m^2/g$. The BET (Brunauer-Emmett-Teller) method is a method well-known to a person skilled in the art. It is described in particular in "The Journal of the American Chemical Society", vol. 60, page 309, February 1938 and corresponds to the international standard ISO 5794/1 (Annex D). The specific surface measured according to the BET method corresponds to the total specific surface, that is to say that it includes the surface formed by the pores.

The expression "particles of free powder" is understood to denote particles which are not grouped together in the aggregate or agglomerate form.

A subject matter of the present invention is thus a process for the manufacture of particles of free polyamide-based powder impregnated with at least one cosmetic or pharmaceutical agent, said process comprising the following successive stages:
  dropwise addition or addition by spraying of said cosmetic or pharmaceutical agent in the liquid state to particles of free powder with stirring, so that the cosmetic or pharmaceutical agent represents at least 25% by weight of the powder particles, said particles being porous and having an SSA of greater than $8\ m^2/g$
  stopping the addition before the powder particles begin to agglomerate,
  maintaining the stirring for at least 5 minutes, preferably at least 20 minutes, then
  recovering the free powder obtained impregnated with said cosmetic or pharmaceutical agent.

Advantageously, said particles of free powder have a mean diameter by volume within the range extending from 3 to 12 m, preferably from 5 to 10 µm.

According to a preferred embodiment of the invention, said polyamide-based particles are chosen from particles of polyamide, copolyamide, copolyesteramide and their mixtures.

The term "polyamide-based particles" (the polyamide being a homopolyamide or copolyamide) within the meaning of the invention is understood to mean the condensation products of lactams, of amino acid and/or of diacids with diamines and, as a general rule, any polymer formed by units connected to one another via amide groups.

The particles according to the invention can also result from the copolymerization of lactam(s) with one or mars lactone(s), resulting in a copoyesteramide, as described in the patent EP 1 172 396.

The term "monomer" in the present description of the copolyamides should be taken in the meaning of "repeat unit". The case where a repeat unit of the polyamide is composed of a combination of a diacid and a diamine is special. It is considered that it is the combination of a diamine and a diacid, that is to say the diamine.diacid pair (in equimolar amount), which corresponds to the monomer. This is explained by the fact that, individually, the diacid or the diamine is only a structural unit, which is not sufficient in itself alone to polymerize. In the case where the particles according to the invention comprise at leant two different monomers, known as "comonomers", that is to say at least one monomer and at least one comonomer (monomer other than the first monomer), they form a copolymer, such as a copolyamide, abbreviated to CoPA, or else a copolyesteramide, abbreviated to CoPEA.

Mention may be made, as example of lactams, of those which have from 3 to 12 carbon atoms on the main ring and which can be substituted. Mention may be made, for example, of β,β-dimethylpropiolactam, α,α-dimethylpropiolactam, amylolactam, caprolactam, capryllactam, oenantholactam, 2 pyrrolidone and lauryllactam.

Mention may be made, as example of diacid (or dicarboxylic acid), of acids having between 4 and 18 carbon atoms. Mention may be made, for example, of adipic acid, sebacic acid, azelaic acid, suberic acid, isophthalic sold, butanedioic acid, 1,4-cyclohexanedicarboxylic acid, terephthalic acid, the sodium or lithium salt of sulfoisophthalic acid, dimerized fatty acids (these dimerized fatty acids have a dimer content of at least 98% and are preferably hydrogenated) and dodecanedioic acid HOOC—$(CH_2)_{10}$—COOH.

Mention may be made, as example of diamine, of aliphatic diamines having from 6 to 12 atoms; it can be arylic and/or saturated cyclic. Mention may be made, as examples, of hexamethylenediamine, piperazine, tetramethylenediamine, octamethylenediamine, decamethylenediamine, dodecamethylenediamine, 1,5-diaminohexane, 2,2,4-trimethyl-1,6-diaminohexane, polyoldiamines, isophoronediamine (IPD), methylpentamethylenediamine (MPDM), bis (aminocyclohexyl)methane (BACM), bis(3-methyl-4-aminocyclohexyl)methano (BMACM), meta-xylylenediamine, bis(p-aminocyclohexyl)methan and trimethylhexmethylenediamine.

Mention may be made, a example of amino acid, of α,ω-amino acids, such as aminocaproic acid, 7-aminoheptanoic acid, 11-aminoundecanoic acid, n-heptyl-11-aminoundecanoic aid and 12-aminododecanoic acid.

Mention may be made, as example of lactone, of caprolactone, valerolactone and butyrolactone.

The monomer(s) preferentially used in the invention s or are chosen from lactams, such as, for example, lauryllactam, caprolactam, oenantholactam, capryllactam or their mixtures. Preferably, use is made of lauryllactam alone or as a mixture with caprolactam.

Preferably, the polyamide-based particles according to the invention comprise, before impregnation, a content, as molar percentage, of polyamide 12 within the range extending from 50% to 100%, preferably from 80% to 100%.

Preferably, said particles of polyamide-based powder are obtained at least in part by anionic polymerization, by seeding with an inorganic or organic filler, of lactam(s) and/or lactone(s) in solution and/or in suspension in an organic liquid. Reference may be made, for example, to the processes described in the documents EP0 192 515 and FR 2 910 900. Advantageously, said porous particles in the present invention are spheroidal. They are preferably chosen from the powders sold under the Orgasol® brand. According to the invention, the cosmetic or pharmaceutical agent is an agent which improves the condition of the keratinous substances of human beings, such as the human skin, hair, eyelashes or the nails, or else the lips of the face.

Preferably, said at least one cosmetic or pharmaceutical agent is liquid at the temperature at which the addition is carried out in the process according to the invention. The addition can be carried out at any temperature, as soon as the cosmetic or pharmaceutical agent is liquid at the time of the addition. The addition temperature is carefully chosen by a person skilled in the art so that the cosmetic agent is both liquid and stable (does not decompose at the addition temperature). Advantageously, the addition is carried out at ambient temperature, for example at a temperature within the range from 15 to 25° C., using a cosmetic or pharmaceutical agent which is liquid and stable at this temperature. Specifically, the cosmetic or pharmaceutical agent is introduced in the liquid state, that is to say in the form of a pure liquid or of a solid dissolved or solubilized in a solubilizing agent, such as water, polyols or glycerides. When it is dissolved, the content of the cosmetic or pharmaceutical agent in the process according to the invention is that of the agent plus its solubilizing agent.

In addition to the cosmetic or pharmaceutical agent, the powder particles obtained according to the process of the invention can thus include water, for example purified or of thermal origin. According to this specific embodiment of the invention, said particles comprise water.

Said at least one cosmetic or pharmaceutical agent used in the present invention is chosen from moisturizing agents, astringent, antiseptic agents, anti-inflammatories, antimicrobial agents, anti-cellulitic agents, antiseborrheic agents, mattifying agents, absorbing agents, antidandruff agents, anti-wrinkle agents, antioxidant, agents for combating free radicals, smoothing agents, lubricants, softeners, colorants, antisun agents, anti-irritants, antirosacca agents, healing agents, decongestant, regenerating agents, deodorants, scenting agents, antiperspirants, depilatory agents, agents which stimulate the growth of head hair or eyelashes, depigmenting agents, film-forming agents, adherent agents, fixing agents, pigmenting agents, pearlescent agents, self-tanning agents, pigmentation photodynamic agents, vitamins and their mixtures.

The cosmetic or pharmaceutical agents used in the present invention are those conventionally used in the cosmetic and dermatological fields. They are generally based on organic or inorganic molecules. Cosmetic or pharmaceutical agents based on organic molecules are particularly well suited to the present invention.

Mention may be made, in particular, as examples of cosmetic or pharmaceutical agents, of:
  moisturizing and nourishing agents, such as amino acids (glycine, alanine, threonine, citrulline), components of swat (lactic acid, sodium chloride, urea, serine); α-hydroxy acids (AHAs), sugars (mannose, fructose, galactose, N-acetylglucosamine); and unsaponifiable products resulting from natural oils, such as jojoba oil, olive oil or soybean oil; or natural or synthetic ceramides (such as oleoyldihydrosphingosine);
  astringents, such as aluminum salts, and pore-reducing agents, such as those described in the patent application WO 02/32392;

antiseptic agents, such as trichlorocarbanilide (TCC), dichlorophen, bromochlorophen, triclosan, or essential oils, such as thyme, rosemary, savory or oregano;

anti-inflammatories or anti-irritants, such as α-bisabolol, dipotassium glycyrrhizinate, glycyrrhetinic acid and its derivatives, ellagic acid, ursolic acid, ibuprofen, naproxen, fenoprofen, carprofen, ketoprofen, steroidal anti-inflammatories, such a cortisone, pregnenolone or desonide, and mixtures of alkanolamines and tyrosine, such as those described in the patent application EP 1 192 939, or rosemary extracts;

antimicrobial, bacteriostatic, bactericidal, fungistatic or fungicidal agents;

anticellulitic agents, such as caffeine, escin, lecithin, forskolin, carnitine tetrahydroxypropylethylenediamine or the natural extract of Chenopodium quinoa seeds;

antiseborrheic agents, such as iminodibenzyl or fluorene derivatives, such as described in the U.S. Pat. No. 6,355,687, substituted secondary amine derivatives, such as described in the U.S. Pat. No. 6,355,686, glucuronic acid and glucosamine derivatives and their salts, such as described in the patent application BP 1 219 296, or the combination of niacinamides with a salicylic acid $C_{11}$-$C_{20}$ alkenyl ester or alkyl, such as is described in the patent application WO02/067889;

keratolytic or prodesquamating agents, for example α-hydroxy acids, β-hydroxy acids, α-keto acids, β-keto acids, retinoids and their esters, retinal, retinoic acid and its derivatives;

mattifying agents or absorbing agents, such as clay, kaolin, antilipases or ethyl lactate;

antidandruff agents, such as zinc pyrithione;

antiwrinkle agents or smoothing agents, such as proteins or their hydrolysates, collagen, elastane, vegetable oils, polyunsaturated fatty acids or firming agents, antioxidants, such as butylated hydroxytoluene (BHT), butylated hydroxyanisole (BHA), propyl gallate octyl gallate, carotenoids such as β-carotene, lycopene or canthaxanthin, ubiquinone, pentaerythrityl tetra(dibutyl-hydroxy-cinnamate), vitamin E, Trolox, vitamin C and its derivatives;

agents for combating free radicals, such as vitamin B, caffeine, mannitol, lemon balm extracts and certain enzymes, such us superoxide dismutases, glutathione peroxidase or catalases;

softeners or lubricants, mach as silicones;

colorants of mineral, animal (cochineal), vegetable (naphthoquinones, anthraquinones) or synthetic origin;

antisun agents, UV-A and/or UV-B screening agents, pigments or nanopigments; mention may be made as screening agents, of p-aminobenzoic acid and its derivatives (glyceryl, ethyl or isobutyl esters); anthranilates (such am o-aminobenzoate or its alkyl esters); salicylates (amyl, phenyl, benzyl or dipropylene glycol esters); cinnamic acid derivatives (amyl or benzyl esters); dihydroxycinnamic acid derivatives (umbelliferone); trihydroxycinnamic acid derivatives (esculetin); hydrocarbons (stilbene); dibenzalacetone or benzalacetophenone; coumarin derivative; hydroxy- or methoxy-substituted-benzophenones; tannic acid and its derivatives; benzophenones and any other antisun screaming agent conventionally used in the cosmetic and/or dermatological field, much as benzylidinecamphor, benzene-1,4-[di(3-methylidene-10-camphorsulfonic)] acid or [4-(3-methylidenecamphor)phenyl]trimethylammonium methyl sulfate, 2-ethylhexyl 2-cyano-3,3-diphenylacrylate or dibenzoylmethane, and their mixtures; mention may be made, as pigments or nanopigments, of zinc and/or titanium oxides ($TO_2$, $ZnO_2$);

antirosacea agents which are active with regard to microcirculation, vasoconstrictors, such as witch hazel, or fluid extracts of sweet clover, hawthorn, Ruscus, dextran sulfate, rhatany or horse chestnut;

healing agents, such as sucralfate or Centella asiatica;

decongestants, such as cornflower water, azulene or α-bisabolol;

regenerating agents, much as horsetail;

deodorants, such as zinc ricinoleate, lactic or tartaric acid derivatives, or antiseptics, such as those already described;

scenting agents and aromatic materials of vegetable or animal natural origin or of synthetic origin;

antiperspirants, such as aluminum and zirconium salts, potassium alum, extracts of leaves of buchu, witch hazel;

depilatory agents, such as sulfur-comprising organic derivatives or thioglycolic and thiolactic acid alts;

agents which are inhibitors of the growth of head hair or body hair, such as the serine proteases described in the U.S. Pat. No. 6,407,056, caffeic acid, quercetin, propyl gallate, nordihydroguaiaretic aid or NDGA, indomethacin, eflornithine hydrochloride, the plant extracts as described in the U.S. Pat. No. 6,171,595, such as extracts of clove, rosebud, burnet, gambier, and the like, the compounds described in the U.S. Pat. No. 6,075,052, tetramisole, sodium orthovanadate, levamisole, disodium cromoglycate, vanadium nitrate and gallium nitrate, a described in the U.S. Pat. No. 6,020, 006, and the compounds described in the patents U.S. Pat. No. 4,885,289, U.S. Pat. No. 4,720,489, U.S. Pat. No. 5,132,293, U.S. Pat. No. 5,096,911, U.S. Pat. No. 5,095,007, U.S. Pat. No. 5,143,925, U.S. Pat. No. 5,328,686, U.S. Pat. No. 5,440,090, U.S. Pat. No. 5,364,885, U.S. Pat. No. 5,411,991, U.S. Pat. No. 5,648,394, U.S. Pat. No. 5,468,476, U.S. Pat. No. 5,475,763, U.S. Pat. No. 5,455,608, U.S. Pat. No. 5,674,477, U.S. Pat. Nos. 5,728,736 and 5,652,273 and in the patent applications WO 94/27586, WO 94/27563 and WO 98/03149. Use may also be made of juniper extracts, such as described in the U.S. Pat. No. 6,375,948;

antidandruff agents, such as zinc pyrithione;

agents which inhibit head hair loss and also stimulators of the growth of head hair or eyelashes, such as minoxidil, biotin, finastride, 2,4-diaminopyrimidine N-oxide, panthenol and its derivatives, T-flavanone, or more generally any plant extract having an anti-Sa-reductase type 1 or 2 activity;

depigmenting agents, such as hydroquinone, ascorbic acid and its derivatives, magnesium ascorbyl phosphate or kojic acid;

film-forming, adherent or fixing agents pigmenting agents, inorganic pigments or synthetic pigments;

pearlescent agents of organic or inorganic natural origin or synthetic origin;

self-tanning agents, such as dihydroxyacetone or DHA;

pigmentation photodynamic agents, such as tyrosine derivatives or melanin precursors, such as indole-5,6-quinone;

vitamins, such as vitamin A, B, B2, B3, B5, B6 or B5, vitamin C or K, vitamin F or H, vitamin PP, vitamin D, D2 or D3, and their derivatives;

and their mixtures.

According to a preferred embodiment of the present invention, said at least one cosmetic or pharmaceutical agent is chosen from moisturizing agents, that is to say emollients, humectants, relipidizing agents and their mixtures. Mention may specifically be made, among moisturizing agents, of emollients which, as they are occlusive, retain water on human skin, the lips of the face or the superficial body growths, such as ceramides, essential oils and the like; and humectants, which capture water, such a polyols, for example glycero propylene glycol, sorbitol, and the like. Preferably, said at least one cosmetic or pharmaceutical agent is chosen from polyols, such as glycerol or propylene glycol; glycerides, such as triglycerides; sodium hyaluronate; lactic acid; lipids; ceramides, such as ceramide-3; and their mixtures.

Advantageously, said at least one cosmetic or pharmaceutical agent comprises a compound with a chemical formula identical to that of a skin compound, that is to say a compound naturally present in healthy human skin. Advantageously, said at least one cosmetic or pharmaceutical agent results from biofermentation. This production process is based on natural fermentation, a biotechnology process consisting in allowing yeast to ferment, which yeast will produce spontaneously the cosmetic or pharmaceutical agent, for example hyaluronic acid. Thus, the cosmetic or pharmaceutical agent obtained exhibits the highest available degree of purity since it is without any residue of solvent or impurity. Furthermore, these biotechnological processes make it possible to control the distribution of the molecular weights of the cosmetic or pharmaceutical age. For example, the use of sodium hyaluronate resulting from biotechnology, with a molecular weight strictly of less than $10^6$ daltons, preferably of less that 350 000 daltons, preferably of less than 250 000 daltons, makes it possible to increase the level of sodium hyaluronate which can be incorporated in the porous particles. This range of controlled molecular weight also makes possible better penetration of the cosmetic agent, in this case sodium hyaluronate, into the upper layers of the epidermis, as is shown by measurement of corneometry, of imperceptible water loss, and of cohesion of the skin. In particular, the impregnation according to the process of the invention of porous particles impregnated with such a sodium hyaluronate dissolved in water makes it possible to introduce water encapsulated in said porous particles into anhydrous formulations, such as lipsticks, compact powders or cast foundations.

Another subject matter of the present invention is particles of free polyamide-based powder which are capable of being obtained according to the process described above, said particles being porous, having an SSA of greater then 8 $m^2/g$ and having a content of at least 25% by weight of at least one cosmetic or pharmaceutical agent other than water.

Advantageously, said at least one cosmetic or pharmaceutical agent represents at least 40% by weight of the powder particles.

Preferably, said particles have a mean diameter by volume within the range extending from 3 to 12 µm, preferably from 5 to 10 µm. Preferably, said polyamide-based particles are chosen from particles of polyamide, copolyamide, copolyesteramide and their mixtures. Advantageously, said polyamide-based particles comprise a content, as molar percentage, of polyamide 12 of at least 50%. According to a preferred embodiment of the present invention, said particles of polyamide-based powder are obtained at least in part by anionic polymerization, by seeding with an inorganic or organic filler, of lactam(s) and/or lactone(s) in solution and/or in suspension in an organic liquid. More preferably still, said particles are spheroidal.

The advantage of using porous powders predominantly comprising polyamide 12 as support for cosmetic or pharmaceutical agents is their very high compatibility with the constituents of the surface of the skin. The molecular structure of the chains of polyamide 12 is similar in several respects to that of the ceramides, the main constituents of the upper layers of the epidermis. The chains of polyamide 12 comprise long hydrocarbon segments (units) comprising 12 carbon atoms, forming lipophilic fatty chains similar to those of the lipid constituents of the skin. They provide high compatibility with the skin: softness, no irritation, excellent persistence and a degree of penetration into the horny layer facilitated by a particle size of 5 to 10 µm. Finally, the amide functional groups of the chains of polyamide 12 are polar functional groups which establish hydrogen bonds with the amide functional groups of the ceramides of the skin, reinforce the compatibility between the particles of the invention and the surface of the skin and prolong the adhesion of the particles to the surface of the skin. This makes it possible to prolong the contact between the powders charged with cosmetic or pharmaceutical agent and the surface of the skin and optimizes the effectiveness of these agents at the surface of the skin.

In particular, the microporous powders which predominantly comprise polyamide 12 (molar content of polyamide 12 of greater than or equal to 50%) and which have a mean particle size of less than or equal to 12 µm have properties of optimum compatibility with the upper layers of the horny layer.

The powder particles according to the invention constitute supports for very stable cosmetic agents which can generally comprise up to 50% by weight of cosmetic or pharmaceutical agents with regard to the total weight of impregnated powder. They are very stable with regard to temperature (melting point of greater than 130° C.) and make it possible to use the active principles in processes which exceed 90° C., such as cast foundations or lipsticks.

Advantageously, said at least one cosmetic or pharmaceutical agent is, a described above, chosen from moisturizing agents, astringents, antiseptic agents, anti-inflammatories, antimicrobial agents, anti-cellulitic agents, antiseborrheic agents, mattifying agents, absorbing agents, antidandruff agents, anti-wrinkle agents, antioxidants, agents for combating free radicals, smoothing agents, lubricants, softeners, colorants, antisun agents, anti-irritants, anti-rosacea agents, healing agents, decongestants, regenerating agents, deodorants, scenting agents, antiperspirants, depilatory agents, agents which stimulate the growth of head hair or eyelashes, depigmenting agents, film-forming agents, adherent agents, fixing agents, pigmenting agents, pearlescent agents, self-tanning agents, pigmentation photodynamic agents, vitamins and their mixtures.

Preferably, said at least one cosmetic or pharmaceutical agent is chosen from moisturizing agents, that is to say chosen from emollients, humectants, relipidizing agents and their mixtures. Preferably, said at least one cosmetic or pharmaceutical agent is chosen from polyols, such as glycerol or propylene glycol; glycerides, such as triglycerides; sodium hyaluronate; lactic acid; lipids; ceramides, such as ceramide-3; and their mixtures.

According to an advantageous embodiment of the present invention, said at least one cosmetic or pharmaceutical agent comprises a compound having a chemical formula identical to that of a skin compound, that is to say a compound present naturally in healthy human skin. For example, the ceramides are a lipid family of great biological importance. The external layer of the skin (stratum corneum) provides the primary protection of the akin. It is 65% composed of ceramides (lipids). Extracellular ceramides make possible the cohesion of the stratum corneum and the formation of the epidermal barrier, and also participate in the desquamation process. In particular, ceramide-3 supports the function of the main lipids of ceramide and performs the function of effective barrier against dehydration of the skin. However, with ago, the body's own production of ceramides continually diminishes. The skin gradually loses its ability to bind and store water. It thus loses its suppleness, its elasticity and its tonicity. Thus, according to a specific embodiment of the invention, powder particles having a high content of ceramide-3 can overcome this deficiency of ceramides of the skin. According to another example, hyaluronic acid is a major participant in the regulation of the water content of the skin and it is consequently essential in maintaining youthful skin. This natural component of the connective tissue is today synthesized and can thus be incorporated in the particles according to the invention in order to form a moisturizing aqueous film on the skin. According to yet another example, lactic acid and lactates are natural components of human beings, with multiple functions: moisturizing, humectant, antimicrobial, pH-regulating or lightening, the optically active L+ form of lactic acid being particularly effective.

Preferably, said at least one cosmetic or pharmaceutical agent results from biofermentation. This can be the case, for example, for lactic acid, L(+)-lactic add, hyaluronic acid, or ceramide-3, which products can be synthesized by biofermentation, with all the abovementioned advantages in terms of purity, control of molecular weights and the like.

Another subject matter of the present invention is the use of powder particles as defined above in cosmetic, pharmaceutical or perfumery products. Said powder can be used in particular in the manufacture of a product comprising a cosmetic or pharmaceutical agent having an improved diffusion, that is to say enhanced and/or prolonged, into the stratum corneum after topical application of said product to the skin.

Another subject matter of the present invention is a cosmetic, pharmaceutical or perfumery composition, characterized in that it comprises particles as defined above. Said composition can, in particular, be a colored, colorless or transparent product, chosen from the following products:
  makeup products for the human face and body, such as foundation, tinted cream, loose or compact powder, eye-shadow, mascara, eyeliner or lipstick;
  care products for the human face and body, such as cream, milk, lotion, mask, scrubbing product, cleansing and/or makeup removing products, deodorants, antiperspirants, shaving products or hair-removing products;
  hair products, such as shampoos, products for the shaping of the hair, products for retaining the hairstyle, anti-dandruff products, products for combating hair loss, products for combating dryness of the hair, hair dyes or bleaching products;
  perfumery products, such a fragrance, milk, cream, or loose or compact scented powder.

EXAMPLES

The following examples illustrate the present invention without limiting the scope thereof in the examples, unless otherwise indicated, all the percentages and parts are expressed by weight.

Example 1: Impregnation Process According to the Invention

Device:
  Use is made of a mixing reactor equipped: with a stirrer-wall scraper, a disperser-lump breaker, a system for regulating the temperature, a system which make it possible to operate under vacuum (vacuum pump, nitrogen trap), and with flushing with an inert gas, such as nitrogen (optional according to the cosmetic or pharmaceutical agents).
Preparation of the Powder:
  The powder is introduced into the reactor;
    the vacuum is applied in order to degas the powder (30 mm of mercury);
    the powder is stirred (60 rev/min) and the vacuum is maintained for 30 minutes;
    the reactor is isolated.
Preparation of the Active Material:
  According to the nature of the cosmetic or pharmaceutical agent, it is or is not necessary to carry out a solubilization. If the cosmetic or pharmaceutical agent is liquid, relatively non-viscous and sufficiently wetting it can be directly impregnated on the powder. If not, it has to be dissolved, just like the solid agents, in a solubilizing agent, as described above, exhibiting cosmetic properties, such as purified water, thermal water, glycerol, propylene glycol, glycerides, essential oils, and the like. It is preferable to limit the amount of solubilizing agent to typically from 2 to 3 times the volume of cosmetic or pharmaceutical agent.
Impregnation of the Active Material:
  The solution of active principle is introduced dropwise into the reactor, the powder continuing to be stirred.
  The optimum degree of impregnation is reached when the powder particles remain free and retain their initial flowability, that is to say retain the sane particle size distribution as before impregnation. They must not begin to agglomerate.
  For unstable and oxidation-sensitive active principles, the introduction is carried out while flushing with nitrogen.
  Once the introduction has been completed, the powder continues to be stirred for 30 minutes.
  In order to prevent caking of the powder, it is possible to use a disperser or other equivalent rapid-stirring systems.
  Particles of free powder are obtained which are highly charged with cosmetic or pharmaceutical agent(s).

Example 2: Particles of Free Powder Comprising a High Content of Cosmetic or Pharmaceutical Agent(s) According to the Invention

TABLE 1

| | Example 2.1 | Example 2.2 |
|---|---|---|
| Cosmetic or pharmaceutical agent | Ceramide-3 | Lactic acid |
| Powder particles | Copolyamide PA 6/12 (20%/80% in moles)-10 μm SSA > 8 m$^2$/g | Polyamide PA12 5 μm SSA > 8 m$^2$/g |
| Solubilizing agent | Olive glycerides | Water |
| Drying | no | no |
| Content of cosmetic agent(s) in the particles of free powder | 25% (Ceramide-3 + Olive glycerides) | 40% lactic acid |
| Function of the agent | Anti-aging, restores the horny layer | Exfoliant, greasy skin regulator |

The PA6/12 and PA12 powder particles respectively used for the manufacture of the impregnated particles of free powder of examples 2.1 and 22 are spheroidal particles of the Orgasol® brand; the diameter shown in μm is the mean diameter by volume. The particles of PA6/12 are obtained according to the process described in the document WO 2008/087335, and the particles of PA12 are obtained according to the process described in the document EP 0 192 515.

The impregnated particles of free powder of examples 2.1 and 2.2 according to the invention respectively have the same particle size and the same specific surface as the PA 6/12 and PA12 powder particles respectively not impregnated with cosmetic agent. In example 2.1, the solubilizing agent for the ceramide-3 results from mixtures of triglycerides, diglycerides and monoglycerides, obtained by esterification of fatty acids of vegetable origin (olive oil in particular). This solubilizing agent is a lipophilic compound which exhibits a high affinity for the skin and which exhibits a light and non-greasy feel. In addition to its cosmetic properties, this solubilizing agent is used according to the invention to solubilize cosmetic agents which ma particularly difficult to solubilize, such as ceramides, in particular ceramide-3. The process according to the invention thus makes it possible to introduce, into porous particles of free powder, ceramides which will subsequently be genuinely available for the upper layers of the epidermis. The effectiveness of these particles according to the invention is demonstrated (see tests of effectiveness in example 4.1) in a foundation composition formulation (see example 3.1).

In example 2.2, the lactic acid results from biofermentation. In these particles of free powder according to the invention, the combination of lactic acid resulting from biotechnology and of porous particles predominantly comprising polyamide 12 makes it possible to increase the effectiveness of the cosmetic product which comprises them, in particular by virtue of the high content of lactic acid particles (40% instead of 20% in the impregnated particles of the prior art). Tests of effectiveness of these particles show that there is a synergy between the porous powders predominantly comprising polyamide 12 and lactic acid with regard to the control of the sebum at the surface of the skin. The effectiveness of these particles according to the invention is demonstrated (see tests of effectiveness in example 4.2) in a makeup-removing milk composition formulation (see example 3.2).

Finally, the particles according to the invention (examples 2.1 and 2.2) do not comprise any trace of solvent harmful to the skin.

The particle size distribution of the powders in the present description, in particular in the examples and comparative examples, is measured using a particle sizer of Coulter LS230 brand. It makes it possible to obtain the particle size distribution of the powders, from which it is possible to determine the mean diameter and the width of the distribution or the standard deviation of the distribution. The particle size distribution of the powders according to the invention is determined according to the usual techniques using a Coulter LS230 particle sizer from Beckman-Coulter. It is possible, from the particle size distribution, to determine the mean diameter by volume with the logarithmic calculation method, version 2.11a of the software, and the standard deviation, which measures the narrowing in the distribution or the width of the distribution around the mean diameter.

Example 3: Compostions Comprising Particles According to the Invention

Example 3.1: Manufacture of a Cast Foundation According to the Following Formulation

TABLE 2

| Phase | INCI | % |
|---|---|---|
| A | Arachidyl alcohol, Behenyl alcohol, Arachidyl glucoside | 2.00 |
|  | Cetyl palmitate | 0.50 |
|  | Cetearyl alcohol | 0.30 |
|  | $C_{18-21}$ Alkane | 4.00 |
|  | $C_{13-15}$ Alkane | 2.00 |
|  | Neopentyl glycol diheptanoate | 3.00 |
|  | Dimethicone | 1.50 |
|  | Polyglyceryl-3 diisostearate | 1.00 |
|  | Ethylhexyl methoxycinnamate | 4.00 |
|  | Butylmethoxydibenzoylmethane | 0.50 |
| B | Aqua | q.s. for 100 |
|  | EDTA | 0.1 |
|  | Glycerol | 2 |
|  | Methylpropanediol | 4 |
|  | Magnesium aluminum silicate | 0.4 |
|  | Cetearyl sulfate | 0.2 |
|  | Xanthan gum | 0.15 |
| C | Mica | 1.5 |
|  | CI77499 | 0.1 |
|  | CI77491/2/9 | 0.4 |
|  | CI77492 | 1.5 |
|  | CI77891 | 6 |
| D | Example 2.1 | 3.00 |

The Ingredients of phase A are weighed out, charged to a melting pot and heated at 110-115° C., while mixing at a constant rate. It is confirmed that the phase is homogeneous and then it is cooled to 85-90° C. The ingredients of phase B are then added one by one while continuously mixing. Before continuing, it is confirmed that the mixture is homogeneous. During this time the powders of phase C are mixed. Phase C is then added to the melting pot while mixing at a constant rate until the combined mixture is homogeneous. The temperature is maintained at 85-90° C. The ingredients of phase D are added one by one and mixing is carried out at a constant rate until the combined mixture is homogeneous. Casting is carried out in appropriate metal molds while maintaining the mixture at 85° C. After cooling, a cast foundation is obtained.

Example 3.2: Composition of a Makeup-Removing Milk According to the Present Invention with D and not According to the Present Invention with D1 or D2

TABLE 3

| Phase | INCI | % |
|---|---|---|
| A | Aqua | q.s. for 100 |
|  | Disodium EDTA | 0.15 |
|  | Hydroxypropyl guar | 0.05 |
|  | Xanthan gum | 0.15 |
|  | Glycerol | 3.00 |
| B | PEG 8 stearate - cetearyl ethylhexanoate - isopropyl myristate - glyceryl stearate - stearyl heptanoate - cetyl alcohol - butyl stearate - cetyl palmitate - sorbitan sesquioleate - stearic acid - aqua - potassium hydroxide - BHA | 8.00 |

TABLE 3-continued

| Phase | INCI | % |
|---|---|---|
| | Cetearyl alcohol | 1.50 |
| | Butyrospermum parkii butter | 2.00 |
| | Isononyl isononanoate | 4.00 |
| | Macadamia ternifolia seed oil | 8.00 |
| | β-Sitosterol | 0.20 |
| | Phenoxyethanol - methylparaben ethylparaben - butylparaben propylparaben - isobutylparaben | 0.80 |
| C | Aqua | 5.00 |
| | Imidazolidinyl urea | 0.30 |
| | Sodium cocoamphoacetate | 2.00 |
| D | | |
| For example 3.2 or D1 | Particles of free powder of example 2.2 | 2.00 |
| | Nylon 11 (Rilsan T NAT BHV COS) | 2.00 |
| For comparative example 1 or D2 | Polyamide PA12 (5 μm, SSA > 8m²/g) (Orgasol ®) | 1.20 |
| | Lactic acid | 0.80 |
| | Nylon 11 | 2.00 |
| For comparative example 2 | Nylon 11 | 2.00 |

All the components of phase A are mixed. Phase B is added with stirring, followed by phases C and D (or D1 or D2) in succession. The pH of the makeup-removing milk obtained is controlled.

Example 4: Tests of Effectiveness on a Composition According to the Invention

The compositions of example 3 are tested by panels of trained experts.

Example 4.1

The composition of example 3.1 according to the invention (cast foundation) is compared with a placebo composition (comparative example 3) in which the particles of free powder according to the Invention have been replaced by the same content of talc (3%). The imperceptible water loss (also known as transepidermal water loss (TEWL)) obtained after use of these two compositions is compared. The transepidermal water is that which diffuses through the skin before coming back up to its surface. It then evaporates therefrom and is lost. The more damaged the horny layer, the greater the imperceptible water loss.

The well-known method of the Tewameter®, by means of a Tewameter® 300 device (Courage+Khazaka electronic GmbH), is used.

TABLE 4

| Measurement of the variation (%) in transepidermal water loss (TEWL) | After 7 days of use | After 15 days of use | After 30 days of use | After 60 days of use |
|---|---|---|---|---|
| Comparative example 3 | −1% | −2% | −3% | −3% |
| Example 3.1 | −6% | −8% | −10% | −12% |

The daily application to the face of the composition of example 3.1 results in an improvement of the barrier function of the skin, which is characterized by a decrease in the imperceptible water loss TEWL of 12% after 60 days of use of the foundation of example 3.1. The reduction in TEWL is only 3% for the same placebo foundation composition not comprising particles according to the invention (comparative example 3).

The level of sebum obtained after use of these two compositions (comparative example 3 and example 3.1) is compared by the Sebumeter® method using a sebumeter of Sebumeter® 815 brand, Courage+Khazaka GmbH.

TABLE 5

| Measurement of the variation (%) in the level of sebum | After 7 days of use | After 15 days of use | After 30 days of use | After 60 days of use |
|---|---|---|---|---|
| Comparative example 3 | +2% | +2% | +3% | +3% |
| Example 3.1 | +4% | +8% | +14% | +18% |

The daily use of the composition of example 3.1 continuously improves the hydrolipidic film of the skin, as is shown by the change in the level of sebum. For comparative example 3, the level of sebum remains unchanged.

The variations in the parameter "smooth appearance of the skin" obtained after use of these two compositions (comparative example 3 and example 3.1) are compared by the method of skin surface evaluation by mean of a Visioscan VC 98 device (Courage+Khazaka electronic GmbH) used for the in vivo and 3D analysis of the surface of the skin. The parameter measured by the image analysis is the SESm (skin smoothness) which is calculated from the mean wrinkle width and the mean wrinkle depth. The lower the value of SESm, the smoother the appearance of the skin.

TABLE 6

| Measurement of the variation (%) in the parameter "smooth appearance of the skin" | After 7 days of use | After 15 days of use | After 30 days of use | After 60 days of use |
|---|---|---|---|---|
| Comparative example 3 | +3% | +5% | +6% | +6% |
| Example 3.1 | +8% | +11% | +12% | +14% |

The use of the foundation of example 3.1 according to the invention increases the smooth appearance of the skin by 14% after 60 days of daily use. According to the nature of the skin, the increase in the smoothness of the akin can reach 30% with the composition of example 3.1 according to the invention. The placebo formulation (comparative example 3) improved the smooth appearance of the skin by only 6%, a plateau reached after 30 days.

The impregnated particles according to the invention (example 2.1) have a long term effectiveness with regard to the reduction of the rough appearance of the skin and with regard to the reduction in the depth of the wrinkles. FIG. 1 is a graph representing a cross section of skin through three wrinkles referenced 1, 2 and 3 (on the abscissa) with different depths (on the ordinate). The level (depth) of the wrinkles is represented before (in dark gray, 5) and after (in light gray, 6) 60 days of use of the foundation of example 3.1. It is noticed, on this graph, that the depth (6) of the wrinkles is significantly reduced after 60 days of use in comparison with the depth (5) of the wrinkles before use of the composition according to the invention, to approach the surface (4) of the skin (represented by a horizontal line on the top part of the graph).

Example 4.2

The composition of example 3.2 according to the invention (makeup-removing milk) is compared with two compositions:

a composition, referred to as comparative example 1, in which the particles of free powder which are charged with cosmetic agent (lactic acid) of the present invention (of example 3.2) have been replaced with equivalent contents of lactic acid and of free powder based on polyamide of the same type but not impregnated with the lactic acid, a composition, referred to as comparative example 2, which does not comprise particles of free powder which are charged with cosmetic agent.

The amount of sebum on the surface of the skin is measured before the application of the makeup-removing milk, then 2 hours after the first application and, finally, after a week of daily application.

The amount of sebum at the surface of the skin is measured according to the well-known measurement method of the sebumeter (the reference of the sebumeter used is: Sebumeter 815, Courage+Khazaka GmbH). This is a direct measurement of the accumulation of the sebum on the skin.

TABLE 7

| Measurement | Example 3.2 | Comparative Example 1 | Comparative Example 2 |
| --- | --- | --- | --- |
| Variation (reduction in %) in the level of sebum 2 hours after application of the makeup-removing milk | −30% | −20% | −5% |

The use of the makeup-removing milk of example 3.2 according to the invention reduce the sebum on the surface of the skin by at least 30%. The use of the makeup-removing milk of comparative example 1 reduces the sebum by only 20% and that of comparative example 2 reduces the sebum by only 5%.

This difference in effectiveness between the makeup-removing milk compositions of example 3.2 and comparative example 1 is maintained even after storing for 6 months. This confirms the stability of the particles of free powder comprising a high content of cosmetic or pharmaceutical agent according to the invention in the formulations comprising them.

The particles of free powder comprising a high content of cosmetic or pharmaceutical agent according to the invention "boost" or enhance the effectiveness of the agent present in them. Furthermore, it is noticed that the action observed for the formulations comprising particles according to the example 2.2 of the invention is not followed by a rebound effect since, after makeup removal, the level of sebum does not increase again but, on the contrary, remains stable and corresponds to the level desired for a normal skin (about 190 µg/cm$^2$), also after 7 days of daily use of the makeup-removing milk of example 3.2, as is shown in table 8.

TABLE 8

| | Before application of the makeup-removing milk of example 3.2 | 2 hours after the application of the makeup-removing milk of example 3.2 | After 7 days of daily use of the makeup-removing milk of example 3.2 |
| --- | --- | --- | --- |
| Level of sebum (µg/cm$^2$) | 265 | 188 | 185 |
| Classification | greasy skin (>220) | normal skin (100-220) | normal skin (100-220) |

The invention claimed is:

1. A particle consisting of free polyamide-based powder, and at least one cosmetic or pharmaceutical agent other than water, in a solubilizer, said particle being porous, with an SSA of greater than 8 m$^2$/g and a content of at least 40% by weight of said at least one cosmetic or pharmaceutical agent other than water, wherein the cosmetic or pharmaceutical agent is in the form of a pure liquid or as a solid dissolved in a solubilizer containing no solvent harmful to the skin, said solubilizer consisting of purified water, thermal water, glycerol, propylene glycol, a glyceride or an essential oil, said polyamide-based particle having a content, as molar percentage, of polyamide 12 of at least 50%, said cosmetic or pharmaceutical agent consisting of lactic acid, a ceramide or a mixture thereof.

2. The particle as claimed in claim 1, in which said particle has a mean diameter by volume within the range from 3 to 12 µm.

3. The particle as claimed in claim 1, in which said polyamide-based particle is particles of polyamide, copolyamide, copolyesteramide or their mixtures.

4. The particle as claimed in claim 1, in which said particle of polyamide-based powder is obtained at least in part by anionic polymerization, by seeding with an inorganic or organic filler, of lactam(s) and/or lactone(s) in solution and/or in suspension in an organic liquid.

5. The particle as claimed in claim 1, in which said particle is spheroidal.

6. The particle as claimed in claim 1, in which said at least one cosmetic or pharmaceutical agent is a compound having a chemical formula identical to that of a skin compound.

7. The particle as claimed in claim 1, in which said at least one cosmetic or pharmaceutical agent results from biofermentation.

8. The particle according to claim 1, wherein the solubilizer is glycerol, propylene glycol, or a triglyceride.

9. A cosmetic, pharmaceutical or perfumery composition, comprising the particle of claim 1.

10. The cosmetic, pharmaceutical or perfumery composition as claimed in claim 9, said composition being a colored, colorless or transparent product selected from the group of products consisting of:
   makeup products for the human face and body, foundation, tinted cream, loose powder, compact powder, eye-shadow, mascara, eyeliner, lipstick;
   care products for the human face and body, cream, milk, lotion, mask, scrubbing product, cleansing and/or makeup removing products, deodorants, antiperspirants, shaving products, hair-removing products;
   hair products, shampoos, product for the shaping of the hair, products for retaining the hairstyle, antidandruff products, products for combating hair loss, products for combating dryness of the hair, hair dyes, bleaching products;
   perfumery products, fragrance, milk, cream, and loose or compact scented powder.

11. The cosmetic, pharmaceutical, or perfumery composition of claim 9 having an enhanced and/or prolonged diffusion into the stratum corneum after topical application of said product to the skin.

12. A process for the manufacture of particles of free polyamide-based powder impregnated with at least one cosmetic or pharmaceutical agent according to claim 1, said process comprising the following successive stages:
   adding dropwise or by spraying said cosmetic or pharmaceutical agent in the liquid state to particles of free polyamide base powder with stirring, so that said cosmetic or pharmaceutical agent represents at least 40% by weight of the powder particles, said particles being porous and having a specific surface area (SSA) of greater than 8 m$^2$/g wherein the cosmetic or pharmaceutical agent is in the form of a pure liquid or as a solid dissolved in a solubilizer containing no solvent harmful to the skin, said solubilizer consisting of purified water, thermal water, glycerol, propylene glycol, a glyceride or an essential oil, said polyamide-based particle having a content, as molar percentage, of polyamide 12 of at least 50%, said cosmetic or pharmaceutical agent consisting of a lactic acid, a ceramide or a mixture thereof, stopping the addition before the powder particles begin to agglomerate, maintaining the stirring for at least 5 minutes, then recovering the free powder obtained impregnated with said cosmetic or pharmaceutical agent.

13. The process as claimed in claim 12, in which said at least one cosmetic or pharmaceutical agent is liquid at the temperature at which the addition is carried out.

14. The process as claimed in claim 12, in which said particles have a mean diameter by volume within the range from 3 to 12 μm.

15. The process as claimed in claim 12, in which said polyamide-based particles are chosen from particles of polyamide, copolyamide, copolyesteramide and their mixtures.

16. The process as claimed in claim 12, in which said particles of polyamide-based powder are obtained at least in part by anionic polymerization, by seeding with an inorganic or organic filler, of lactam(s) and/or lactone(s) in solution and/or in suspension in an organic liquid.

17. The process as claimed in claim 12, in which said particles are spheroidal.

18. The process as claimed in claim 12, in which said particles comprise water.

19. The process as claimed in claim 12, in which said at least one cosmetic or pharmaceutical agent comprises a compound with a chemical formula identical to that of a skin compound.

20. The process as claimed in claim 12, in which said at least one cosmetic or pharmaceutical agent results from biofermentation.

* * * * *